United States Patent [19]

Chaudoin et al.

[11] Patent Number: 4,958,456
[45] Date of Patent: Sep. 25, 1990

[54] INSECT ERADICATION

[75] Inventors: James J. Chaudoin, Norco; Michael R. Linford, Villa Park, both of Calif.

[73] Assignee: Isothermics Incorporated, Long Beach, Calif.

[21] Appl. No.: 465,431
[22] Filed: Jan. 16, 1990
[51] Int. Cl.$^5$ ............................................. A01M 1/20
[52] U.S. Cl. ..................................... 43/124; 43/132.1
[58] Field of Search ............................. 43/124, 132.1

[56] References Cited

U.S. PATENT DOCUMENTS 4,648,202 3/1987 Renth .................................. 43/132.1
4,688,349 8/1987 Renth .................................. 43/132.1
4,807,391 2/1989 Bokiau .................................. 43/131
4,817,329 4/1989 Forbes ................................ 43/132.1

Primary Examiner—Richard K. Seidel
Assistant Examiner—James Miner
Attorney, Agent, or Firm—Grant L. Hubbard

[57] ABSTRACT

A method of killing insects by dispersing boric acid, neat or in mixture with other ingredients, e.g. diatomaceous earth or extenders, etc., into spaces and onto surfaces known or believed to be inhabited by insects to be killed and thereafter heating the spaces and surfaces onto which boric acid has been dispersed to a temperature of at least 110° F. for a period of at least about one-half hour or greater until substantially all insects in said spaces and on such surfaces are dead.

11 Claims, No Drawings

INSECT ERADICATION

FIELD OF THE INVENTION

This invention relates to the eradication of insects in building structures. More specifically, this invention relates to the eradication of space-dwelling insects, i.e. insects which traditionally dwell in building spaces, rather than inside building structural members, such as roaches, ants, fleas, etc.

Man's battle with insects predates the earliest recorded history. Indeed, the history of mankind has been shaped in many respects by its continuing competition with insects for food and warmth.

The common cockroach is one of the oldest of the currently living species and one of the species which has demonstrated almost total immunity to man's efforts at eradication. Cockroaches are known throughout the world as domestic pests and are a frequent nuisance, especially in warm temperate and tropical areas. Cockroaches occasionally carry organisms such as bacteria or parasites that produce intestinal diseases, but they are more generally considered to be mechanical carriers of contaminating filth. Since cockroaches are scavengers, they are often found where man is found, i.e. in his buildings and campsites. Early man probably spread cockroaches as he moved about seeking food. Modern commerce has been even more helpful to these unwelcome travellers. An analysis of the distribution of eleven domiciliary species found in the United States and related species found eleswhere suggest that five of these species reached the United States from West Africa and two probably came from the orient and two more probably from Europe. One of those species found in the United States probably originated in the West Indies. Man has been the most important agent in the spreading of cockroaches throughout the world.

Cockroaches are among the most abundant and earliest of the fossilized insects discovered at various localities in North America, France and the U.S.S.R. Some of these fossils are said to date to 345 million years ago, and many are said to date at least 200 million years ago. Probably more time and and wealth is spend in efforts to control or exterminate cockroaches than is spent on any other single class of insects.

Fleas are parasites which live on the exterior of the host. They are bloodsucking insects and important carriers of disease and sometimes are serious pests. As the chief agent transmitting the Black Death, the bubonic plague, in the Middle Ages, they were an essential link in a chain of events which killed a quarter of the population of Europe. Infestations by fleas may cause severe inflammation of the skin and intense itching, and both man and animals may become sensitized after exposure and develop serious allergies. Species that attack man and livestock include cat flea, the human flea, the dog flea, the sticktight flea, the jigger and various minor groups of fleas.

Fleas are believed to be the principal carriers of murine typhus, a rickettsial disease of man originating from rats or mice. Fleas are considered important in the maintenance and spread of many locally restricted infections among rodents and mammals. They are the probable carriers of the filarial worm of dogs and serve as the intermediate host of the common tapeworm, which infects dogs and cats and occasionally children. Pet owners maintain a constant vigilance to prevent the mass infestation of their pets and frequently their homes from fleas, and it is of great health, practical and emotional importance to eradicate fleas as thoroughly as possible.

Ants of various species are frequently attracted to dwellings and industrial buildings and may infest stored foods and generally be an aesthetically obnoxious pest.

Other insects of lesser general importance, but of particular local importance during certain times, seasons and locations, are also known to invade and infest and sometimes to thrive in building structures inhabited by humans, as well as animal shelters.

During the past century, most efforts at control and eradication of structure-dwelling insects has been focused on chemical poisons. Many chemicals are known to be quite effective as insecticides, and some have long-lasting residual insecticidal properties. DDT, for example, is known to be a very effective insecticide, having residual insecticidal properties for weeks, months or even years after application; however, DDT is also known to cause severe ecological consequences and, consequently, has been banned in the United States and in many other countries. Other insecticides may be highly toxic to insects, but are also highly toxic to humans, pets and warm-blooded animals generally, or have very serious ecological impact. Some kinds of chemical insecticides hydrolyze after exposure to the moisture in the air for a period of time and become benign to human and warm-blooded animals, but may still have very important ecologically damaging residues. Some insecticides are so highly poisonous that they must be used only in the hands of very skilled operators to prevent serious injury or death.

It is, therefore, of great importance that methods be developed to control and eliminate insects which are non-destructive and which are non-toxic and environmentally innocuous. One such method is described in U.S. Pat. No. 4,817,329, issued to Charles Forbes, Apr. 4, 1989, wherein structure-dwelling and ground dwelling insects, e.g. termites, are destroyed by heating the structural elements, or the ground, to a temperature above the temperature which is lethal to the structure- or ground-dwelling insects. This technique is a very important step forward in the control of termites and comparable structure-or ground-dwelling insects; however, the treatment is so expensive and so extreme that it has only limited, if any, applicability to the destruction of space-dwelling insects such as the common cockroach.

A remaining problem, thus, exists with respect to the control and eradication of cockroaches and other space-dwelling insects. Desirably, the solution to this problem will not require such extremely high and long heating periods and will be safe for use in animal and human dwellings and free from significant toxicity. It is to a solution of this problem that the present invention is directed.

SUMMARY OF THE INVENTION

The present invention comprises the treatment of building spaces with boric acid and heat. It has been found that there is a very high synergism between the use of moderate heat, well below that used by Forbes, in combination with boric acid. It has been found, for example, that heating a boric-acid-treated space area to approximately 110° to 115° for a period of about an hour or more, preferably at least about an hour, effects an essentially total eradication of roaches, fleas and other space-dwelling insects.

DESCRIPTION OF THE PREFERRED EMBODIMENT

Boric acid, $H_3BO_3$, is a white crystalline, oxygen-bearing acid of boron found in certain minerals and volcanic waters or hot springs in certain mineral deposits. Boric acid, or salts of boric acid, borates, traces of boron are necessary for growth of land plants and thus indirectly essential for human life. In excessive quantities, however, borates may act as unselective herbicides. The most common source of boric acid is borate, sodium tetraborate or borax, which occurs naturally in salt beds. Boric acid may be obtained by treating borate with sulfuric acid. Boric acid is commonly used as a mild antiseptic for burns and surface wounds and comprises a major ingredient in eye lotions. Among its other important applications is its use as a fire retardant in fabrics.

Wood preservatives containing boric acid and other biologically active compounds are known, see West German Offen. DE No. 2 431 595 and Caceres-Rojas, Hernan, Tecnologia, V. II, No. 59, pp. 8–19 (1969), and as chemisterilants containing boron-compounds have been described, Borkovec, et al, J. Econ. Entomol., 62, No. 6, pp 1472–80 (1969) (abstracts only reviewed).

Boric acid is non-toxic to humans and animals and is ecologically benign in low concentrations.

It has now been found that by applying boric acid, using conventional applicator methods and devices, i.e. dusting boric acid as a conventional insecticide is dusted, spraying a solution or slurry or dispersion of boric acid, etc., coupled with heating to a temperature of at least 110° and preferably about 115°, or higher, complete eradication of space-dwelling insects is accomplished. In carrying out the method, finely powdered boric acid, which is conveniently available commercially, is applied by manual or pneumatic, or other, dusting or spraying techniques in the spaces of a structure to be treated. For example, the boric acid may be dusted over carpets, in drawers, in shelves, and on other surfaces. In addition, by using a nozzle, the boric acid can be dusted inside the wall spaces, between the studs of the building structure, in cracks and crevices where cockroaches traditionally live, and in any other area where insect infestation is considered possible or likely. Once the dusting is complete, the structure is heated to at least 110° or higher, optimally about 115° F. The heating may be accomplished, in most structures, simply by closing the structure and applying sufficient heat, either from an internally built space heater, or by pumping heat in from an external source, such as a hot air blower, etc. The heat is maintained for a period of at least about one hour, and optimally from about one and one-fourth to about two hours, or more. Following this heating, which is, in most instances, not sufficiently high to pose threats to structures, contents, wall coverings, furniture coverings, etc., as is sometimes posed by the Forbes method, complete eradication of space-dwelling insects is accomplished.

This phenomenal unusual synergistic effect was first observed and then proved in laboratory tests.

With male German roaches, a 110° F. temperature for 30 minutes resulted in no synergistic effect of heat on boric acid, despite having such a striking effect with flour beetles (Tribolium) as the test insects. However, roaches, kept on boric acid (100 mg. per petri dish) at 100° F. for 80 minutes were killed. Ten roaches were placed in each of 3 petri dishes: A, 100°, with no boric acid; B, 100° with a film of boric acid; C, room temperature (70° F.), with a film of boric acid. The boric acid was evenly spread on blotter paper snugly fit into the petri dishes.

After the 80-minute heating period, the roaches were periodically examined for another 5 hours. The results are summarized below. KD=Knockdown (the roaches are lying on their backs but are still alive); D=dead; A=alive (standing upright and able to move about).

|   | Boric Acid | Temp. | After 80 Minutes at 100° F. | | | Five Hours after Heating | | |
|---|---|---|---|---|---|---|---|---|
|   |   |   | KD | D | A | KD | D | A |
| A | None | 110° F. | 6 | 0 | 4 | 3 | 4 | 3 |
| B | 100 mg. | 110° F. | 9 | 1 | 0 | 2 | 8 | 0 |
| C | 100 mg. | 70° F. | 0 | 0 | 10 | 3 | 1 | 6 |

The above data show that 110° F. for 80 minutes substantially synergizes the toxic action of boric acid. At least in part, this may be because the roaches in the heated petri dish have visibly much more boric acid all over their bodies than the ones in the unheated petri dish.

Test with *Tribolium confusum*, adult beetles Test No. 1.

Twenty adult Tribolium beetles were put in each of 2 petri dishes, on boric-acid-saturated blotter paper. Dish A was kept at 115° F. for 30 minutes, then removed from the heat and left at room temperature (70° F.). Dish B was not heated. In 24 hours, 11 beetles (55%) were dead in A and none in B.

Test No. 2.

Twenty Tribolium beetles were placed in each of 2 petri dishes, A and B, and kept between 110° F. and 115° F. for 3 hours. Dish A contained 100 mg of boric acid powder and dish B contained no boric acid. At the end of the 3 hours of heating, 13 beetles (65%) were dead in A and none in B. In 18 hours all beetles were dead in A and none in B.

Temperatures of 110° F. or ranging between 110° and 115° F., for periods of time ranging from 30 minutes to 3 hours, caused mortality to Tribolium beetles. Likewise, beetles placed on deposits (100 mg per petri dish) of boric acid for periods of up to 2 days, at room temperature (70° F.), suffered no mortality. But when exposed to heat while on the boric acid deposit, the beetles always suffered complete mortality. Moreover, when heated in the empty petri dish for 2 hours at 110° F. and then placed on a boric acid deposit for 2 days, the beetles suffered a 55% mortality.

In entomology, synergists are substances that, when used with an insecticide, cause the mixture to be more toxic than would be expected from the additive effect of the individual components, e.g. when piperonyl butoxide is added to pyrethrum. The above experiments dealt with 2 agents, neither one of which was lethal when used alone. This is a most striking example of synergism.

In summary, the method of killing insects of this invention is applicable to killing insects in spaces and on surfaces, as distinct from killing insects inside structural components, e.g. wood beams or studs, as described in U.S. Pat. No. 4,817,329. The invention comprises the steps of (a) dispersing boric acid, neat or in mixture with other ingredients, e.g. diatomaceous earth or extenders, et., into spaces and onto surfaces known or believed to be inhabited by insects to be killed and, thereafter, (b) heating the spaces and surfaces onto which boric acid has been dispersed to a temperature of at least about 110° F. for a period of at least about one-half hour or greater until substantially all insects in said spaces and on such surfaces are dead. Desirably the temperature of at least about 110° F. is maintained for at least about one hour or more. Temperatures of from 110° F. to less than about 130° F., e.g. 110°–115°±5° F., are preferably maintained from about one to about three or more hours. These temperature-time regimes effectively kill the insects in boric acid treated areas and, generally, do not damage fabrics, wall coverings, etc., as may be the case with higher temperatures.

The method is particularly applicable to killing roaches which dwell on surfaces inside walls, etc., or in crevices, fleas which dwell on carpet surfaces, ants, etc., which may dwell in crevices or on surfaces.

It will be understood that there are many variables within the parameters provided which are within the spirit and scope of the invention.

Industrial Application

This invention is useful in the insect control industry.

What is claimed is:

1. The method of killing insects in spaces and on surfaces comprising:
    (a) dispersing boric acid into spaces and onto surfaces known or believed to be inhabited by insects to be killed; and, thereafter,;
    (b) heating the spaces and surfaces onto which boric acid has been dispersed to a temperture of at least about 110° F. for a period of at least about one-half hour or greater until substantially all insects in said spaces and on such surfaces are dead.

2. The method of claim 1 wherein the temperature of at least about 110° F. ins maintained for at least about one hour or more.

3. The method of claim 2 wherein the temperature is maintained at from about 110° F. to about 115° F.

4. The method of claim 3 wherein the temperature is maintained at from about 110° F. to about 115° F.

5. The method of killing roaches and fleas in spaces and on surfaces comprising:
    (a) dispersing boric acid into spaces and onto surfaces known or believed to be inhabited by insects to be killed; and, thereafter,;
    (b) heating the spaces and surfaces onto which boric acid has been dispersed to a temperature of at least about 110° F. for a period of at least about one-half hour or greater until substantially all insects in said spaces and on such surfaces are dead.

6. The method of claim 5 wherein the temperature of at least about 110° F. ins maintained for at least about one hour or more.

7. The method of killing surface and crevice dwelling insects in building structures comprising:
    (a) dispersing boric acid into spaces and onto surfaces of the building structure which are known or believed to be inhabited by insects to be killed; and, thereafter,;
    (b) heating the spaces and surfaces onto which boric acid has been dispersed to a temperature of at least about 110° F. and less than about 130° F. for a period of at least about one-half hour or greater until substantially all insects in said spaces and on such surfaces are dead.

8. The method of claim 7 wherein the temperature of at least about 110° F. ins maintained for at least about one hour or more.

9. The method of claim 8 wherein the temperature is maintained at from about 110° F. to about 115° F.

10. The method of claim 7 wherein the boric acid is dispersed in mixture with a solid powder of different composition.

11. The method of claim 7 wherein the boric acid is dispersed in mixture with powdered diatomaceous earth.

* * * * *